United States Patent [19]

Howe

[11] Patent Number: 4,472,138
[45] Date of Patent: Sep. 18, 1984

[54] ORTHODONTIC APPLIANCE

[76] Inventor: Raymond P. Howe, 9477 N. Territorial Rd., Dexter, Mich. 48130

[21] Appl. No.: 372,860

[22] Filed: Apr. 28, 1982

Related U.S. Application Data

[63] Continuation-in-part of Ser. No. 315,101, Oct. 26, 1981, Pat. No. 4,424,032.

[51] Int. Cl.³ .............................................. A61C 3/00
[52] U.S. Cl. ......................................... 433/19; 433/20
[58] Field of Search ................... 433/5, 6, 9, 17, 18, 433/19, 20, 21, 22, 24, 3, 10, 11, 13, 14

[56] References Cited

U.S. PATENT DOCUMENTS

| | | | |
|---|---|---|---|
| 702,805 | 6/1902 | Lindas | 433/5 |
| 1,217,374 | 2/1917 | Walker | 433/21 |
| 1,481,861 | 1/1924 | Eaton | 433/10 |
| 1,849,843 | 3/1932 | Levin | 433/20 |
| 2,930,126 | 3/1960 | Kesling | 433/14 |
| 3,043,007 | 7/1962 | Wallshein | 433/20 |
| 3,494,034 | 2/1970 | Kesling | 433/17 |
| 3,618,214 | 11/1971 | Armstrong | 433/19 |
| 3,793,730 | 2/1974 | Begg et al. | 433/21 |
| 3,798,773 | 3/1974 | Northcutt | 433/19 |
| 3,838,515 | 10/1974 | Paugh et al. | 433/20 |
| 4,242,085 | 12/1980 | Wallshein | 433/14 |
| 4,360,341 | 11/1982 | Dellinger | 433/3 |

FOREIGN PATENT DOCUMENTS

| | | | |
|---|---|---|---|
| 1110363 | 7/1961 | Fed. Rep. of Germany | 433/19 |
| 1079955 | 12/1954 | France | 433/19 |
| 2385381 | 12/1978 | France | 433/19 |
| 594976 | 1/1978 | U.S.S.R. | 433/18 |

Primary Examiner—John J. Wilson
Attorney, Agent, or Firm—Stephenson and Boller

[57] ABSTRACT

An orthodontic appliance for jaw correction comprises positioning structure operatively disposed between the upper and lower arches for correcting the condition. The invention relates to improvements operatively relating the positioning structure to the respective arches.

2 Claims, 9 Drawing Figures

ORTHODONTIC APPLIANCE

This application is a continuation-in-part of Ser. No. 315,101, filed Oct. 26, 1981, now U.S. Pat. No. 4,424,032, issued Jan. 3, 1984.

BACKGROUND AND SUMMARY OF THE INVENTION

The present invention relates to orthodontic appliances and is specifically concerned with a new and improved orthodonic appliance for jaw correction.

An anatomical condition, namely mandibular retrognathia, has a significant incidence among orthodontic patients and involves deviation of the lower jaw position from the norm. This condition may be independent of dental malposition per se, and involves a disposition of the entire lower jaw which is considered to detract from an individual's appearance, and which may be a cuase of improper bite. Specifically the condition may comprise an individual's lower jaw being set posteriorly from what would be considered a more favorable location from the standpoint of appearance and/or bite.

An orthodontic appliance which has been available for correcting this condition in certain circumstances is known as the Herbst appliance. Briefly, the Herbst appliance comprises positioning structure which is operatively disposed between the upper and lower dental arches and which is effective, when applied to an individual over a course of time, for improving the aforementioned condition. Over the course of treatment, the positioning structure is effective to cause the lower jaw to naturally assume a more anterior placement by limiting the posterior displacement of the lower dental arch in relation to the upper dental arch. Other types of appliances have also been addressed to correcting the same problem.

The present invention, in one respect, is directed to an improvement in a Herbst type appliance. A Herbst appliance is limited in application because of the manner by which the positioning structure is operatively related to the respective dental arches. In particular the connections of the positioning structure to the dental arches involves the use of individual bands on individual teeth. Accordingly, the Herbst appliance has been suitable generally only for patients in late adolescence where all permanent teeth including the mandibular first bicuspids have erupted so as to provide adequate structure for the individual bands. The Herbst appliance has not been generally recognized as suitable for treating younger individuals for the reason that they lack a complete set of permanent teeth and therefore do not possess adequate dental structure for application of the appliance. Yet, a very effective treatment time for correcting the jaw is pre- and early adolescence.

The present invention constitutes an improvement over the Herbst appliance in that the appliance of the invention is suitable for application during this very effective pre- and early adolescent treatment time.

The invention provides an appliance suitable for use with individuals who do not possess a full set of permanent teeth, particularly children. It has the advantage of being easily applied to patients regardless of age, provided that at least a certain number of teeth are present, even though not a full set. The invention is also highly effective in that the manner by which the positioning structure is operatively related to a dental arch takes place with the arch being stabilized as a unit.

The possibility also exists in certain patients that attempted correction of the jaw through use of a Herbst appliance may give rise to other problems necessitating correction by way of other treatment procedures. For example, tooth separation and/or rotation may occur in response to usage of a Herbst appliance, due principally to the previously accepted manner of operatively relating the appliance to the individual teeth as explained above. Use of the Herbst appliance may result in permanent damage to the incisor teeth due to fracture. During operation of the appliance, the posterior teeth are disoccluded, and the entire biting force may be directed onto the incisor teeth. This can result in fracture if these teeth are brought together forcefully during biting.

Because the improved appliance of the present invention stabilizes the entire dental arch rather than being connected to two individual teeth of the arch, it can be applied with minimum liklihood that separation, rotation and/or fracture will occur. One portion of the improved appliance is effective to cushion the biting force on the incisor teeth and redistribute it over other teeth as well. In this way the possibility of fracture is significantly lessened. This one portion of the appliance also reacts the corrective forces in such a manner that both separation and/or rotation of individual teeth are much less likely than in the case of the Herbst appliance. The complementary portion of the improved appliance, through stabilization of its arch, is also less likely to cause separation and/or rotation. In addition to possessing these attributes the invention is also versatile enough to be used concurrently with other treatment procedures.

The present invention in its preferred embodiment comprises an acrylic plastic splint which is applied through a bonding agent to the cusps of the teeth of the lower dental arch. The plastic splint has a generally U-shaped configuration forming to the shape of the lower arch and can be readily fabricated in accordance with conventional fabrication techniques. Embedded within the plastic body of the splint, at each lateral side, is a metal insert. Each metal insert has perforations, and during fabrication of the splint the acrylic plastic cures onto the metal inserts with the plastic material filling the perforations so as to lock the inserts in place. The inserts are generally toward the posterior of the appliance, and the anterior portion of the splint preferably includes a reinforcing wire which bridges the span between the metal inserts. Projecting from each insert through the plastic is a pivot which provides a pivot connection to one element of the corresponding positioning structure. The positioning structure takes the form of telescopically engaged elements, with a rod element being pivoted on each pivot of the splint and a corresponding sleeve telescoping onto the rod element and operatively connected to the upper arch. Each rod element has an eyelet fitting onto the corresponding pivot. The end of each sleeve element abuts the corresponding eyelet to limit the rearward displacement of the lower arch in relation to the upper arch, thereby allowing anatomical forces to urge the lower jaw forwardly to the end that it will naturally assume a more anterior position. To assist the splint in reacting the forces and torques which are developed through use of the appliance, it is desirable to provide clasps at the posterior ends of the splint which can be engaged with brackets mounted on molar bands on the lower molars.

The appliance further includes connection of each sleeve element to the upper dental arch by mated connector structures connecting the sleeve to a molar band on an upper molar tooth. The mated connector structures comprise a bracket (double buccal tube) on the outside of the molar band and a fitting on the sleeve. The bracket comprises a pair of tubes, and the fitting comprises a pair of projections which fit into the bracket tubes. The sleeve also includes a pivot joint immediately adjacent the fitting. One projection of the fitting has a circular cross section which fits within a corresponding tube of similar circular cross section. The other tube and corresponding projection have polygonally shaped cross sections.

The foregoing features, advantages, and benefits of the invention, along with additional ones, will be seen in the ensuring description and claims which should be considered in conjunction with the accompanying drawings. The drawings disclose a preferred embodiment of the invention according to the best mode contemplated at the present time for carrying out the invention.

BRIEF DESCRIPTION OF THE DRAWINGS

FIG. 7 is a view similar to FIG. 1 illustrating a further embodiment.

DESCRIPTION OF THE PREFERRED EMBODIMENT

Figure 1:
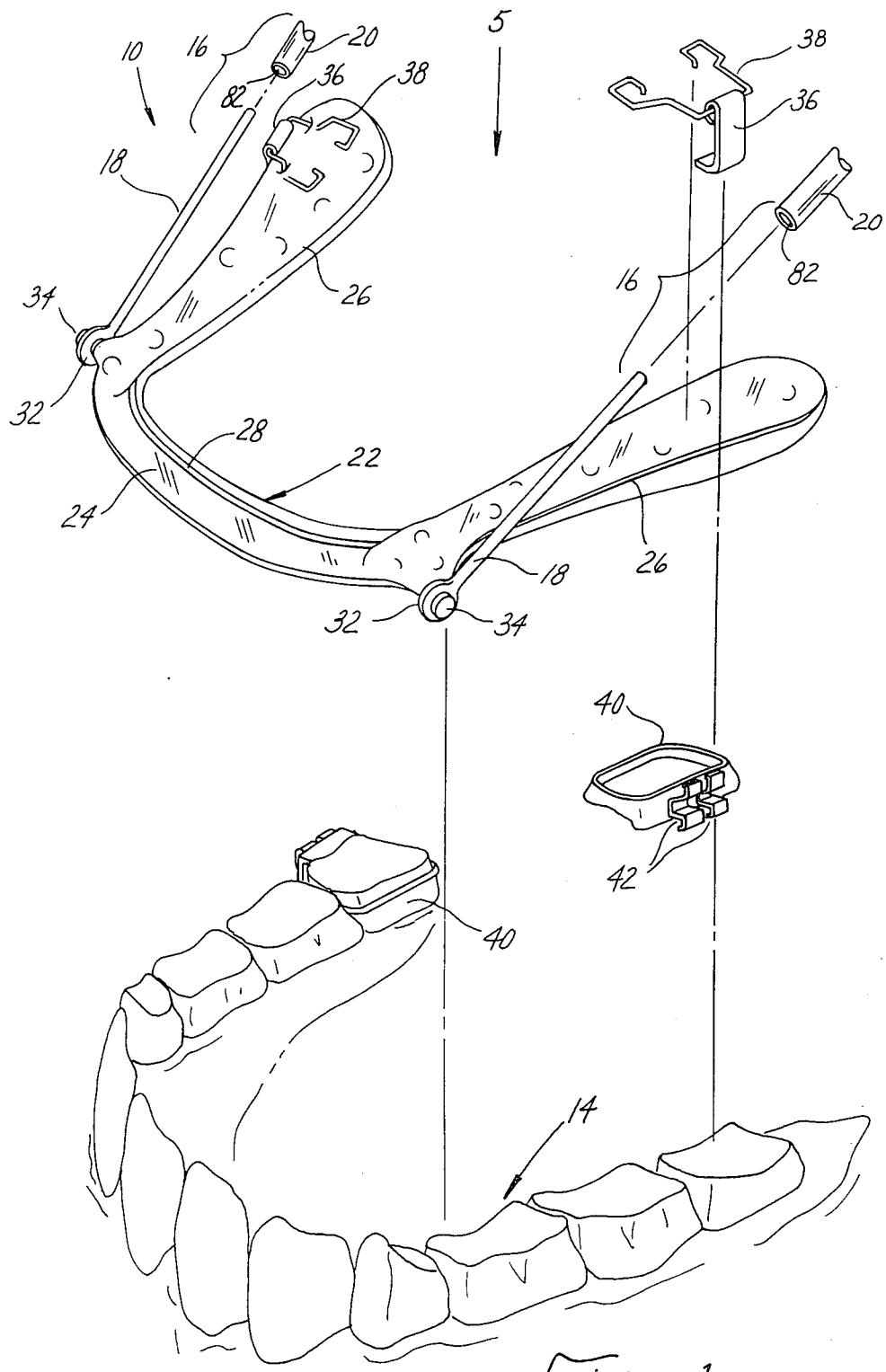
FIG. 1 is a perspective view, partly exploded, illustrating a portion of the orthodontic appliance of the present invention.

The drawings disclose an orthodontic appliance 10 embodying principles of the present invention. The appliance is shown in association with an upper dental arch 12 (FIG. 2) and a lower dental arch 14 (FIG. 1). As mentioned earlier, the appliance includes positioning structure operatively disposed between the upper and lower dental arches for purposes of jaw correction. This positioning structure is generally symmetrically disposed in the lateral sense, comprising two pairs 16 of operatively engaged elements, with the two pairs 16 being disposed on opposite lateral sides of the appliance. Each pair 16 comprises a pair of operatively engaged elements. In the illustrated embodiment one element is a rod 18 while the other element is a sleeve 20. When the appliance is in use each sleeve 20 telescopically engages the corresponding rod 18.

The rods 18 are associated with the lower portion of the appliance which is designated by the general reference number 22. In addition to the pair of rods 18, the lower portion 22 comprises a plastic body 24, a pair of metal inserts 26, and a reinforcing wire 28. The lower portion 22 constitutes a splint having a generally U-shaped configuration corresponding to that of the lower arch 14. The metal inserts 26 are disposed on the lateral sides of the splint and are generally toward the posterior so that when the splint is applied to the lower arch 14, the metal inserts overlie the molar regions. The metal inserts supply rigidifying structure to the splint as well as support of pivots for the rods 18. The reinforcing wire 28 provides rigidifying structure to the plastic 24 along that portion of the splint which bridges the two lateral sides of the U (i.e. toward the front, or anterior, of the splint). The plastic body 24 comprises a self-curing acrylic which can be fabricated in accordance with conventional techniques to be adapted for application directly to the cusps of the teeth of the lower arch 14. During fabrication the metal inserts 26 and the reinforcing wire 28 are encapsulated within the acrylic plastic material so as to become fully embedded within the plastic body upon curing, with the exception of the two pivots which project from the metal inserts to provide pivot points exterior of the plastic body for the rods 18.

Figure 6:
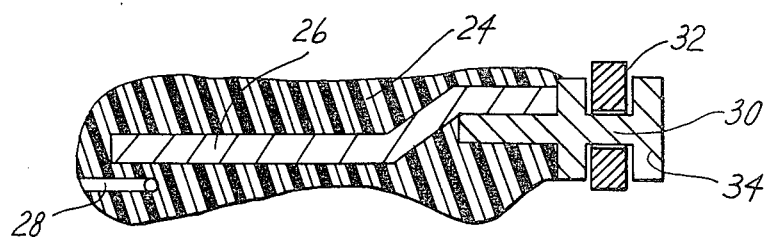
FIG. 6 is a sectional view taken in the direction of arrows 6—6 in FIG. 5.
Figure 1:
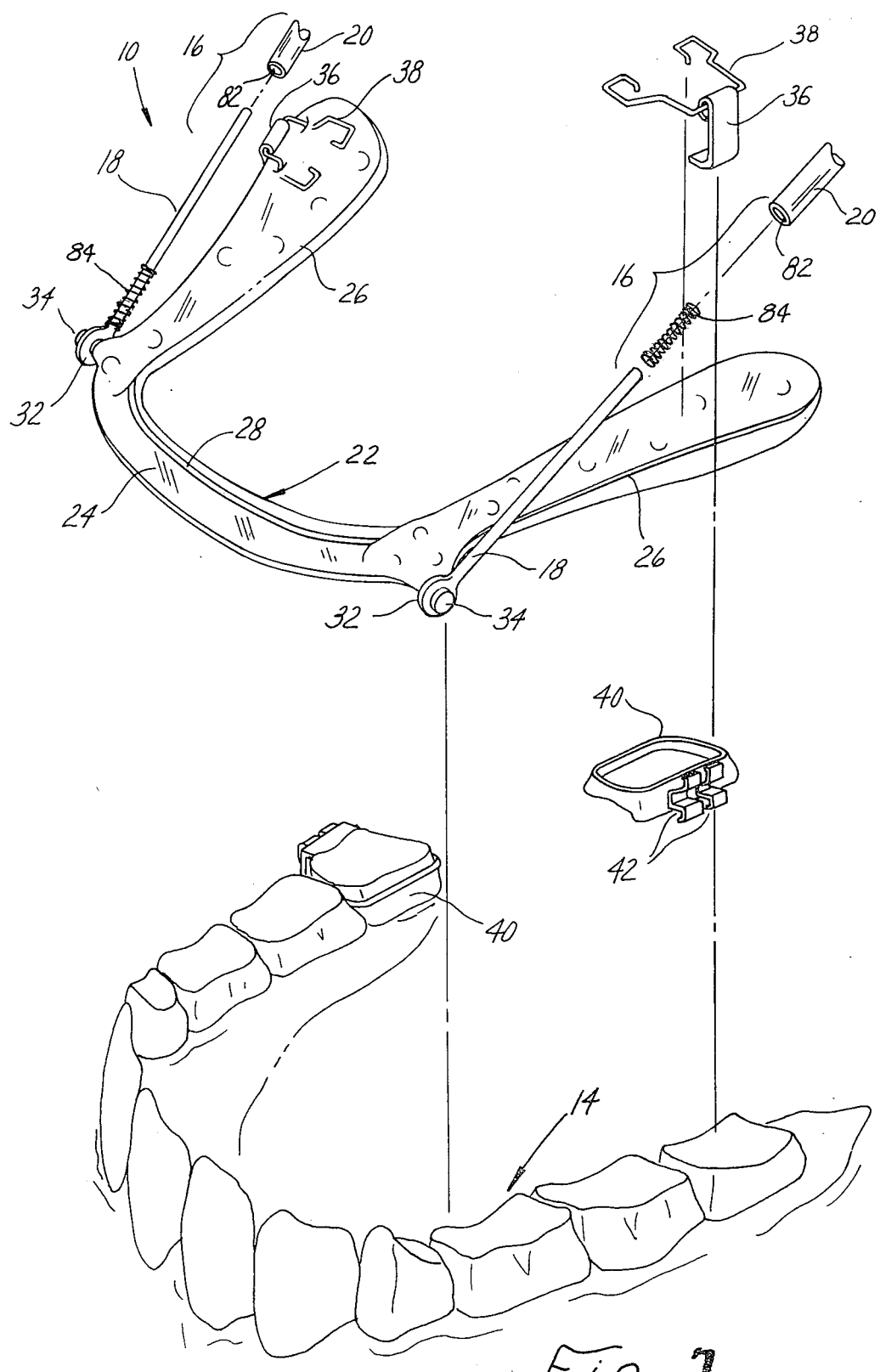

FIG. 6 illustrates details of a pivot wherein a circular cylindrical pivot 30 protrudes from the acrylic plastic body, and the rod 18 has an eyelet 32 having a circular cylindrical hole fitting onto the pivot 30. Each rod is retained on the pivot by means of a head 34. The hole in the eyelet 32 is preferably made a slightly larger diameter than that of the pivot 30 so that the rod, in addition to having a rotational freedom about the axis of the pivot, also has a limited amount of lateral rocking. Details of the manner by which the rod eyelet is retained on the pivot may involve use of any standard procedure such as using a screw and post, riveting, or forming of the head after the eyelet has been placed onto the pivot. It is desirable that the ends of the reinforcing wire 28 overlap the inserts 26; however, it is preferable that the overlapping portions not be in contact with each other.

The splint is applied to the lower arch by use of conventional bonding material between the underside of the splint and the cusps of the teeth.

In order to better react the torques which are developed through use of the appliance, it may be desirable for the splint to include a pair of clasps 36 on opposite sides of the splint. The clasps are metal elements having hooks at the lower end with the top of each clasp being pivoted on the exterior of a formed mounting wire 38, the interior portion of which is embedded in the plastic at the time of fabrication of the splint. Hence, in the completed splint, the clasps 36 overhang the lateral perimeters at the sides of the splint.

In order to utilize the clasps 36 it is necessary for corresponding catches to be applied to the lower arch. This is accomplished by means of molar bands 40 applied to each of the teeth which directly underlie the point at which the clasps mount on the splint. Mounted on each molar band 40 is a bracket having suitable catches 42. With each molar band 40 in place, the splint is applied to the lower arch by placing the plastic body onto the cusps of the teeth and then snapping clasps 36 over the catches 42. The illustrated catches 42 are fashioned in otherwise conventional brackets which are affixed to the outer lateral sides of the molar bands. As will become more apparent from the ensuing description, the use of the appliance develops a downward and forward component of force at each pivot 30. The application of these downward and forward forces to the splint tends to generate torque tending to lift the posterior of the splint, and a purpose of the clasps 36 is to react this torque so that the splint remains securely fixed on the lower arch.

The upper portion of appliance 10 is designated by the general reference numeral 44. Details of the left-hand side of portion 44 can be seen in FIGS. 2, 3, and 4 and it will be understood that the right-hand side is symmetrical, although it is not expressly shown in the drawings. Looking to FIGS. 2 and 3, one can see that each sleeve includes a formed eyelet 46 having a circular hole which is offset from the bore 48 of the sleeve into which the corresponding rod 18 telescopes. A circular pivot pin projects laterally from the body of a connecting fitting 50 and the eyelet 46 fits onto this pivot pin. The eyelet is retained on the pivot pin by means of a head 52. Hence, this arrangement provides a pivot joint for each sleeve. The details of this pivot joint may be similar to those described in connection with the pivot joints for the rods 18 on the lower portion of the appliance.

Each fitting 50 includes a pair of parallel projections 54 and 56 which project generally posteriorly from the body of the fitting. The projection 54 is about one-half the length of the projection 56. The projection 54 has a circular cross section while the projection 56 has a non-circular cross section of polygonal shape. In the example, the cross sectional shape of projection 56 is rectangular. The projection 54 constitutes a support shaft while the other projection constitutes an index pin. Each fitting 50 provides a connector structure for connecting its sleeve 20 to a corresponding mating connector bracket on the upper arch.

Figure 3:
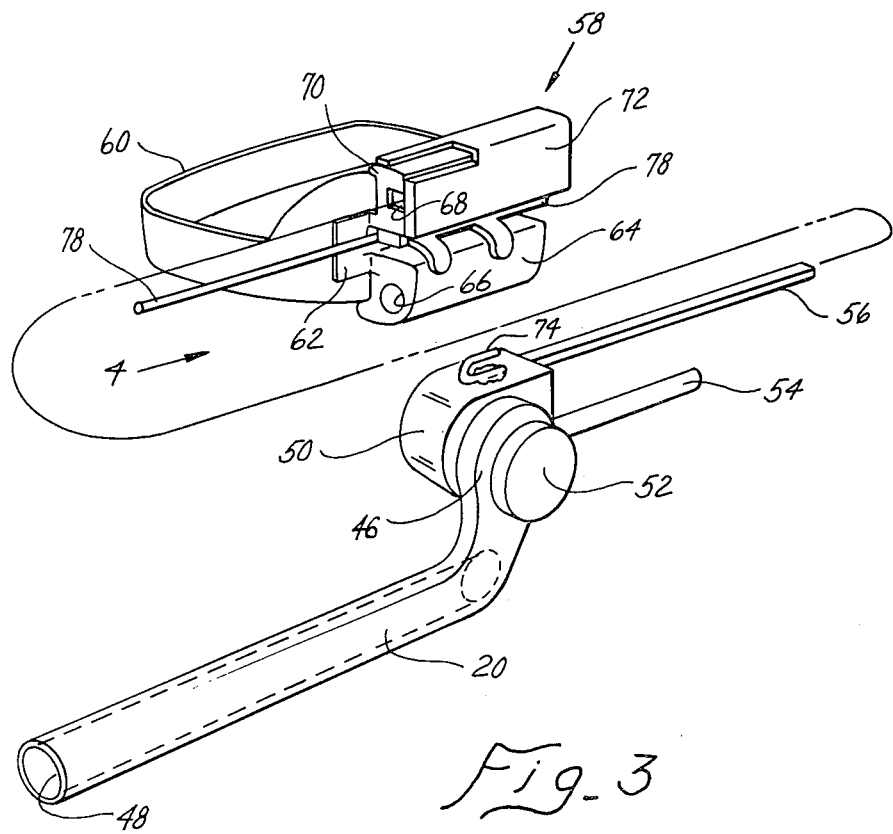
FIG. 3 is a perspective view on an enlarged scale taken within circle 3 of FIG. 2 and showing the component parts in disengaged relationship.
Figure 4:
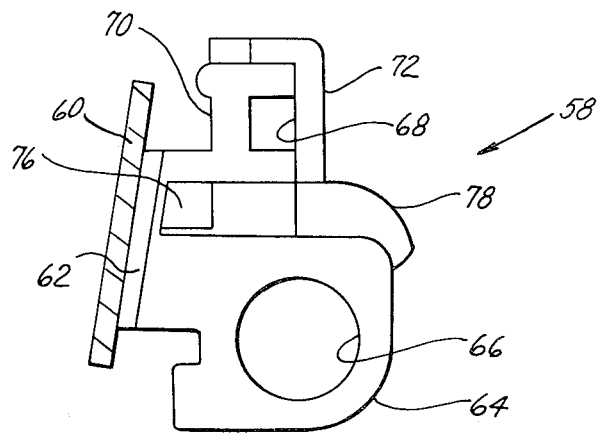
FIG. 4 is a view taken in the direction of arrow 4 in FIG. 3.

The mating connector bracket is designated by the general reference numeral 58 and mounts on a conventional molar band 60 applied to one of the molar teeth, typically the maxillary first permanent molar tooth. Details of connector bracket 58 are shown in FIGS. 3 and 4. The bracket comprises a base 62 disposed against and suitably secured to the outer lateral side of the molar band 60. Supported from base 62 is a bracket body portion 64 having a tube 66. Tube 66 has a circular cross sectional shape for receiving the circular support shaft 54. A second tube 68 is also fashioned on bracket 58 and has a rectangular cross section for receiving the index pin 56. The tube 68 is defined by a body portion 70 having a C-shaped cross section 70 whose throat is covered by a channel-like element 72. The two sockets are parallel.

From this description it will be perceived that the sleeve connector fitting 50 is connected to the molar band connector bracket 58 by inserting the support shaft 54 and the index pin 56 into tubes 66 and 68 respectively as indicated in FIG. 4. The dimensions should be such as to place the axis of the pivot as close as possible to the point at which the two connectors fit together. When the projections 54, 56 are fully inserted into their corresponding tubes 66, 68, the index pin 56 protrudes through the posterior end of tube 68 allowing its distal end to be bent out to parallelism thereby locking the two connectors together. In this way any anterior displacement of the fitting 50 and hence of sleeve 20 is precluded. The use of the two projections 54 and 56 provides for convenient assembly yet provides a strong construction capable of resisting any movement either linearly or rotationally between the two connectors 50 and 58.

Also provided on the body of fitting 50 is a rubber band hook 74. The rubber band hook may be used in conjunction with an additional appliance (not shown). For example, the illustrated hook 74 and its symmetrically opposite counterpart are useful when it is desired to apply anteriorly directed forces. Such forces can be useful in the treatment of a condition in which both the upper and lower jaws are displaced posteriorly. The additional appliance may comprise a face mask for the patient with rubber bands passing through the mouth and attaching to the hooks 74.

It may be perceived that the illustrated connector fitting 58 is generally similar to what is commonly known as a double buccal tube. It differs however from conventional double buccal tubes in that it is in fact a triple buccal tube having a further tube 76. This further tube is provided by lodging an insert 78 into the space between the two body portions 64 and 70 leaving sufficient clearance to define the tube 76. The tube 76 allows one end of an arch wire 78 to be passed through the tube 76 and locked in place. The opposite end of the arch wire connects to the opposite bracket in the same way. Hence the connector bracket 58 is particularly useful for connection of multiple components. Moreover, the design of the connector bracket 58 and mating fitting 50 permits expedient replacement of sleeves 20 whenever desired.

Figure 2:
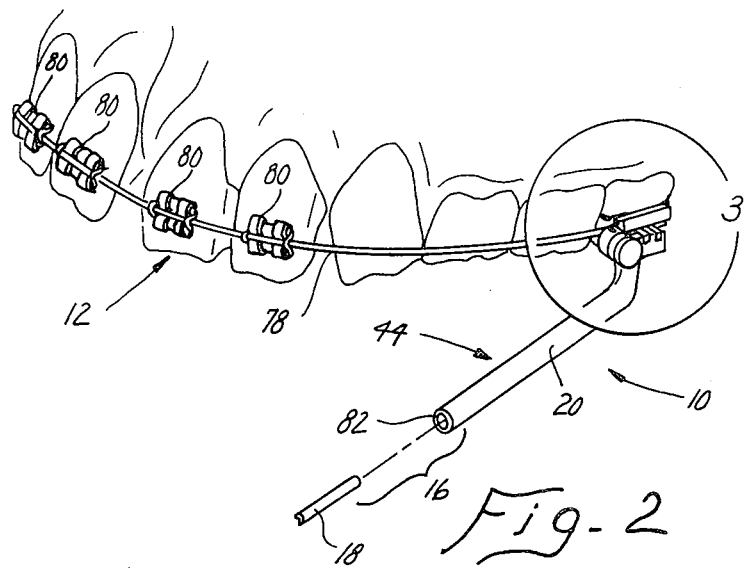
FIG. 2 is a perspective view illustrating a portion of the appliance which cooperates with that shown in FIG. 1.

The arch wire 78 serves to band together other teeth of the upper arch 12 such as through the use of conventional brackets 80 shown in FIG. 2. With this arrangement the entire upper arch has its individual teeth stabilized as a unit. Through the stabilization of the upper arch as a unit by arch wire 78 and through the stabilization of the lower arch as a unit by splint 22, the appliance is effective to promote jaw correction with less likelihood of teeth separation or rotation than in the case of a Herbst appliance.

The appliance is installed by applying the upper and lower portions 22 and 44 individually to their respective arches. After they have been applied the patient may open his mouth without difficulty to a position which will allow each of the two sleeves 20 and its respective rod 18 to be aligned with each other and telescopically engaged. In use the patient will typically not open his mouth sufficiently to allow the rods to become disengaged from the sleeves and hence in the normal course of use the two portions 22, 44 of the appliance remain operatively coupled in telescopic engagement.

The rods 18 are somewhat longer than the bores 48 of the sleeves and hence the distal ends of the rods can project fully through the bores 48, exiting by the open end of each bore 48 near eyelet 46. Maximum telescopic engagement occurs when the distal end 82 of each sleeve 20 abuts the eyelet 32 of the corresponding rod 18. When this happens, it is impossible for the splint 22, and hence the lower arch and jaw, to be displaced posteriorly in relation to the upper arch. The dimensions of the appliance are selected such that when such abutment occurs, the lower jaw is in the desired anterior position which it is intended to assume when the appliance is finally removed. When the appliance is first put to use, the lower jaw is displaced from its uncorrected position because of the action of the appliance in limiting posterior displacement of the lower arch and jaw. Hence, anatomical forces initially attempt to resist the corrective action of the appliance. However, over the course of treatment the anatomy changes in such a way as to accomodate the repositioning of the jaw as established by the appliance so that when the appliance is finally removed the jaw naturally assumes the new corrected position to which it has been set by the appliance. It will be recognized that the corrective forces are active anytime the positioning elements 18, 20 are fully telescoped.

The reader will observe that FIGS. 1 and 2 show the appliance in use with less than the full set of thirty-two permanent teeth. The invention can be applied, not only to adults, but to children as well, and it is not essential for a patient to have a full set of permanent teeth. The invention can be practiced as the sole orthodontic appliance or in conjunction with other orthodontic appliances. Obviously, other variations may also be indulged in.

One such variation may involve an alternative construction for either the upper or lower portion of the appliance, or both. This construction will be particularly useful where the patient has existing brackets on individual teeth possibly on all teeth. These brackets may be mounted directly on the teeth themselves or on bands on the individual teeth. The brackets comprise shapes similar to the brackets 80 shown in FIG. 2. A vertical cross section through the bracket shows the bracket to have a slot, or channel, facing outwardly into which complementary portions of the appliance may be inserted. The complementary portions of the appliance may have a T-shaped cross section. In cross section, the T is rotated 90° from its upright position so that the end of the leg of the T lodges in the channels of the individual brackets. The power portion of the appliance comprises two separate sections, each of T-shaped cross section and these may be considered as corresponding to the two metal inserts 26 in the embodiment of FIGS. 1 and 5. In other words, they are coextensive approximately with the molar regions and each would have an extent similar to the extent of the metal inserts 26. These new elements, however, are disposed between the teeth and the cheeks. The two T-shaped elements can be joined together along the anterior portion of the arch (i.e. along the incisor and cuspid teeth) by any suitable structure corresponding to the bridge 24 and insert 28 of the FIG. 1 and 5 embodiment. This bridging structure may also be attached to individual bands or brackets on these frontal teeth so that this variation operatively relates the appliance to either or both arches.

The lodging of the leg of the T into the slots or channels in the individual brackets may not be suitable alone to retain the appliance. A possible way to secure the appliance to the brackets is by means of apertures extending through the top of the T on both sides of the leg and wires being passed through these apertures and around projecting wings on the brackets thereby ligating the appliance securely to the teeth. Another means of securing the paired T-shaped elements is through the use of elastic ligatures which pass over and around tabs on the T-shaped elements.

Mesial-distal displacement of the T-shaped elements may be avoided by bending tabs on the paired T-shaped elements medially on either side of the individual bracket wings.

Figure 5:
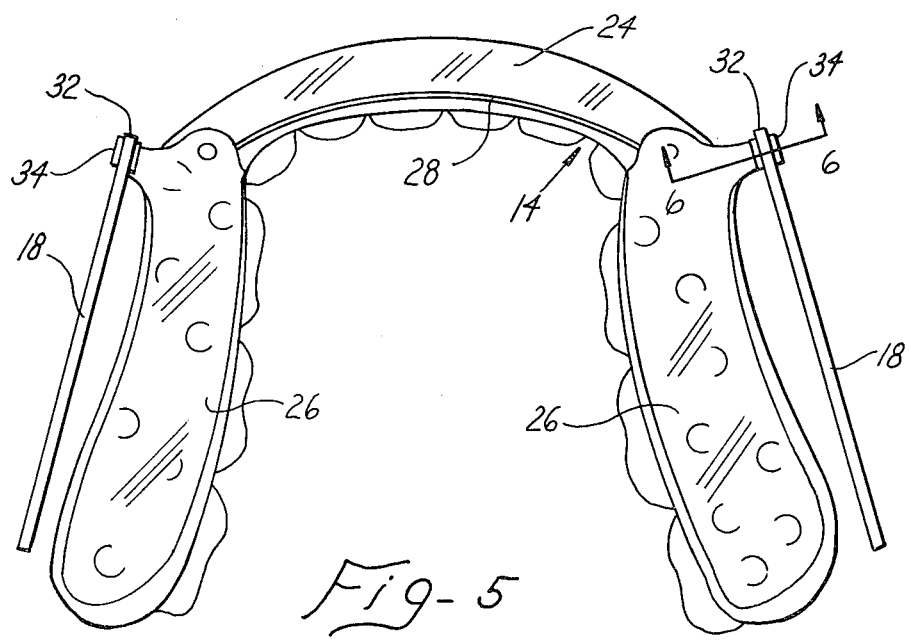
FIG. 5 is a view taken in the direction of arrow 5 in FIG. 1.

The pivotal connections of the rods 18 may be made to the two T-shaped elements in the same vicinity as the rods 18 of FIG. 5 are pivotally connected. For this purpose, a pivot may mount laterally on the top of the T so as to project toward the cheek with the rod eyelet being fitted onto the pivot and secured by a head such as the head 34 in the FIGS. 1 and 5 embodiment. In this way, the modified form of appliance is shown to be suitable for patients which have existing brackets on a number of teeth.

Figure 8:
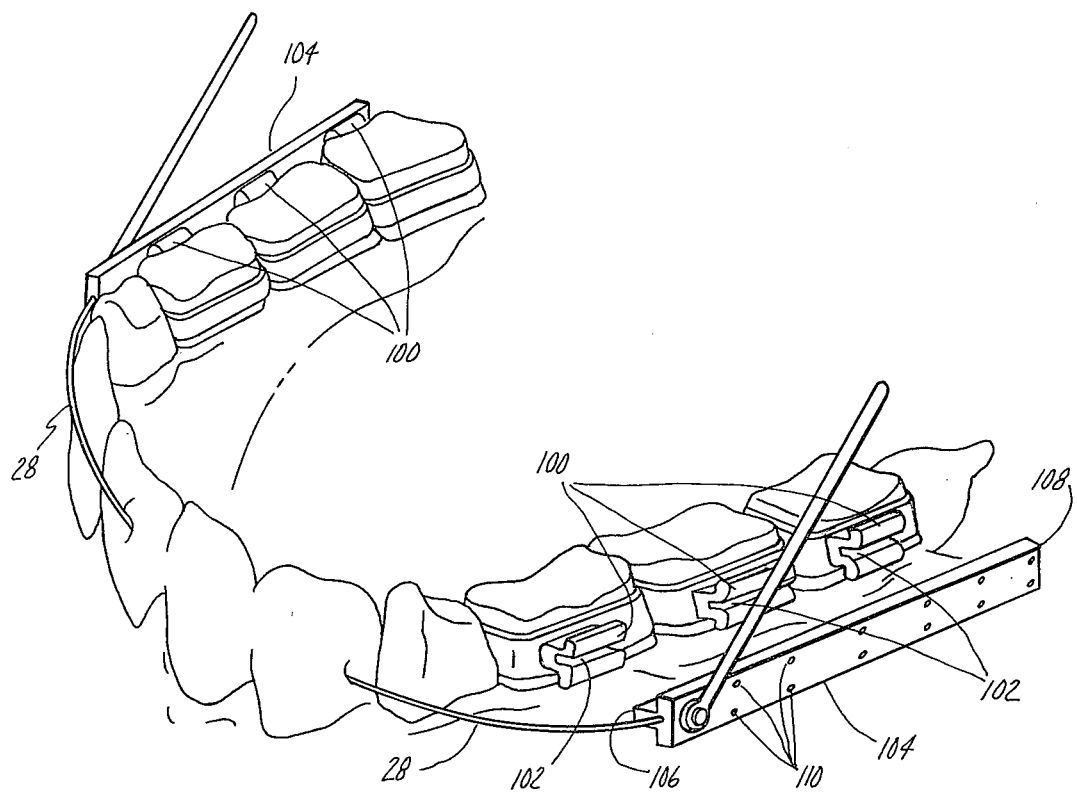
FIG. 8 is a perspective view partly broken away and showing an alternate construction for a portion of the appliance.
Figure 9:
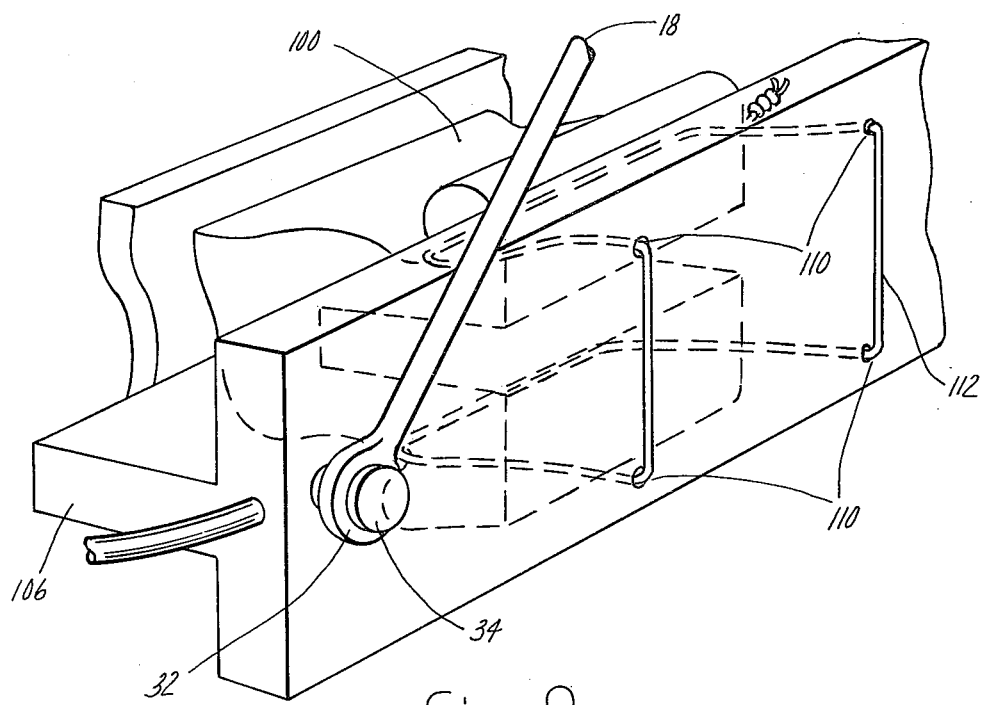
FIG. 9 is an enlarged view of a portion of FIG. 8 showing further assembly details.

FIGS. 8 and 9 illustrate an example of the just described alternate construction as applied to the lower portion of the appliance. In this drawing figure, the reference numeral 100 identifies the brackets mounted on the individual teeth (either directly or by bands), the reference numeral 102 identifies the outwardly facing slot, or channel, in the brackets, and the reference 104 identifies the two T-shaped sections of the appliance on opposite sides of the lower dental arch which are coextensive approximately with the molar regions (i.e. approximately coextensive with the perforated inserts in FIG. 1). The reference numeral 106 designates the leg of the T-shaped sections which is lodged into the slots 102 of the brackets. The reference numeral 108 designates the top of the T, it being noted that the T is rotated 90° from its upright position. The reference numeral 110 designates the apertures extending through the top of the T on both sides of the leg, and the reference numeral 112 designates the ligating wires. The remaining components of the embodiment of FIG. 8 correspond to those illustrated in the preceeding drawing figures and are identified by like reference numerals. As explained above this FIG. 7 embodiment may have advantages for use in certain patients.

FIG. 7 is a perspective view similar to FIG. 1 illustrating a further embodiment of the invention. The embodiment of FIG. 7 is like that of FIG. 1 with the further inclusion of two springs 84. Each spring 84 is operatively associated with a corresponding pair 16 of the operatively engaged positioning elements 18, 20. The springs are so arranged relative to elements 18, 20 as to increasingly compress as the telescopic engagement of the elements 18, 20 increases toward maximum. Without springs 84 there is a greater risk of damage to the appliance or of its separation during the treatment procedure. Because the mounting of the appliance on the upper and lower arches is unyieldable, a patient who either intentionally or unintentionally forcefully engages the telescoping elements such that the distal end 82 of an upper element 20 forcefully abuts the eyelet 32 of a lower element 18 can create appreciable impact forces which can give rise to damage or separation. The inclusion of springs 84 greatly lessens this possibility because large impact forces are avoided.

Various techniques may be used for installing and mounting the springs 84. Our technique involves the placement of the springs over the lower elements 18 so that one end of the spring bears against eyelet 32 while the other end bears against the distal end 82 of the upper element 20. Alternatively the springs may be disposed inside the upper elements 20 at appropriate locations to be abutted by the free distal ends of the lower elements 18. With this latter procedure the springs would be entirely contained within the outer tubular elements 20 whereas in the former case the springs would be exposed. Anchoring of one end of the spring to one of the elements may be appropriate as well. The particular spring characteristics are selected with the objective of alleviating impact in mind, and the springs should not affect the treatment procedure involved for a particular patient because the action of the appliance insofar as treatment is concerned remains the same.

While presently preferred embodiments have been disclosed, it will be appreciated that principles of the invention are applicable to other embodiments.

What is claimed is:

1. In an orthodontic jaw correction appliance of the type comprising positioning means operatively disposed between the upper and lower dental arches, said positioning means including a pair of cooperatively engaged elements one of which is associated with one arch and the other of which is associated with the other arch, the improvement for operatively relating said one element to its associated arch comprising a member disposed to overlie and span the buccal surfaces of at least some of the teeth of the associated arch, said member having a T-shaped transverse cross-section comprising a top portion and a leg portion, a plurality of brackets for mounting on at least some of the teeth whose buccal surfaces the member overlies, said brackets having slots, the leg of said T-shaped member being removably inserted in said bracket slots, and said one element being connected with said member.

2. An arch wire for use in an orthodontic jaw correction appliance of the type comprising positioning means operatively disposed between the upper and lower dental arches, said positioning means including a pair of cooperatively engaged elements one of which is associated with one arch and the other of which is associated with the other arch, and a plurality of brackets for mounting on the buccal surfaces of at least some of the teeth of said one arch, said brackets having slots, said arch wire comprising a member disposed to overlie and span said brackets and provide an operative connection between said brackets and said one of said pair of cooperatively engaged elements, said member having a T-shaped transverse cross section comprising a top portion and a leg portion, the leg of said T-shaped member being removably insertable in said bracket slots, said member having its T-shaped transverse cross section for mesio-distally spanning and operatively engaging with plural teeth via respective brackets thereon.

* * * * *